United States Patent [19]

Omagari et al.

[11] Patent Number: 4,592,341
[45] Date of Patent: Jun. 3, 1986

[54] METHOD AND APPARATUS FOR GUIDING PROSTHESIS

[75] Inventors: Yasuhiko Omagari, Fuchu; Tsutomu Okada, Hachioji, both of Japan

[73] Assignee: Olympus Optical Co., Ltd., Japan

[21] Appl. No.: 731,539

[22] Filed: May 7, 1985

[30] Foreign Application Priority Data

May 23, 1984 [JP] Japan ............................. 59-75410[U]

[51] Int. Cl.[4] ......................... A61B 17/00; A61F 2/04
[52] U.S. Cl. .................................... 128/4; 128/303 R; 128/343; 604/264; 604/285; 623/12
[58] Field of Search ................... 128/3, 4, 5, 6, 7, 328, 128/343, 303 R; 604/264, 280, 285; 623/11, 12

[56] References Cited

U.S. PATENT DOCUMENTS

| | | | |
|---|---|---|---|
| 3,043,309 | 7/1962 | McCarthy | 604/280 X |
| 3,472,230 | 10/1969 | Fogarty | 128/328 |
| 3,674,033 | 7/1972 | Powers | 604/264 |
| 3,811,449 | 5/1974 | Gravlee et al. | 128/343 |
| 4,344,435 | 8/1982 | Aubin | 604/285 X |
| 4,435,853 | 3/1984 | Blom et al. | 128/303 R X |
| 4,466,443 | 8/1984 | Utsugi | 128/4 X |

FOREIGN PATENT DOCUMENTS 59-93502  6/1984  Japan .

Primary Examiner—William H. Grieb
Attorney, Agent, or Firm—Ostrolenk, Faber, Gerb & Soffen

[57] ABSTRACT

A method of and an apparatus for guiding a prosthesis utilizing a flexible sheath in combination with a guide member is taught. Basket forceps assembly which is known in the art is utilized to fracture a calculus located within a coeloma is coupled to the guide member. The guide member carrying the basket is inserted into the coeloma so as to allow it to move past a restriction within the coeloma and without injuring the walls of the coeloma. The guide member, once moved past the restriction, is used as a guide to dispose a prosthesis passed over the guide member at a given location in a smooth manner.

11 Claims, 16 Drawing Figures

F I G. IA
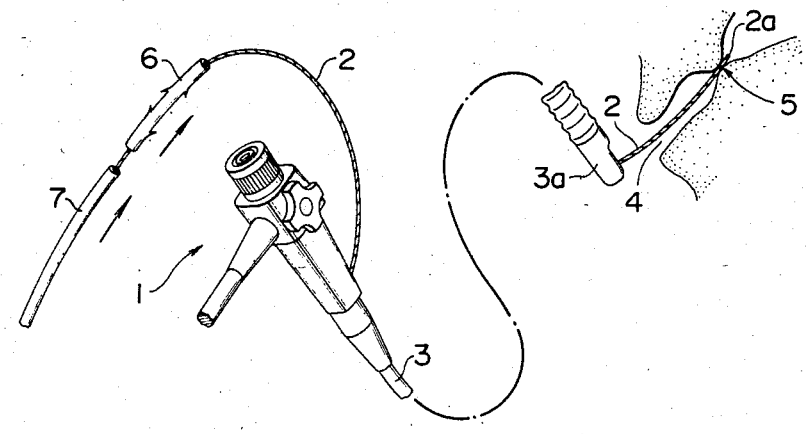
F I G. IB
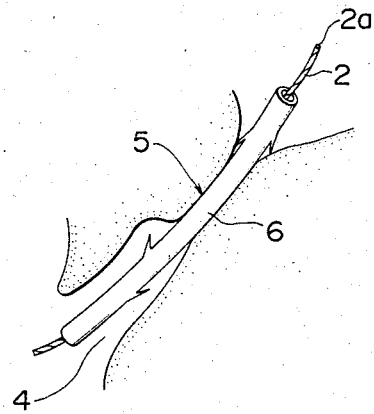
F I G. IC
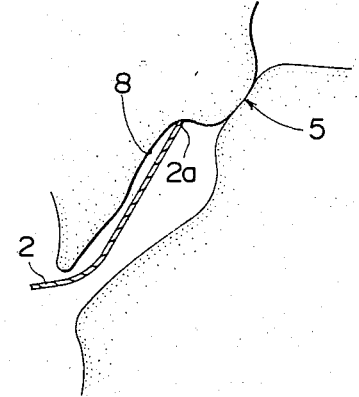

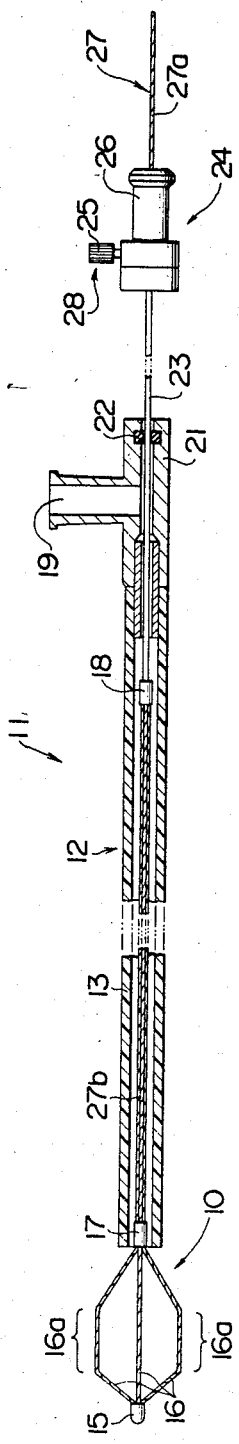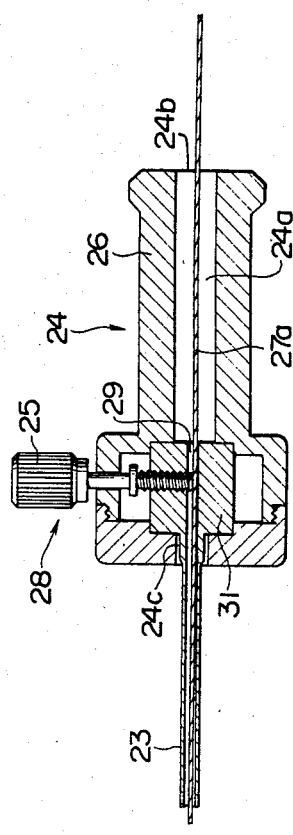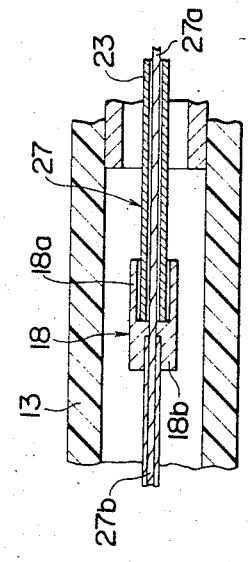
F I G. 2A
F I G. 2C
F I G. 2B

METHOD AND APPARATUS FOR GUIDING PROSTHESIS

BACKGROUND OF THE INVENTION

The invention relates to a method of and an apparatus for guiding a prosthesis, and more particularly, to such method and apparatus which utilizes an endoscope to insert a prosthesis or a tube into coeloma and to retain it at a given location therein.

When an opening of a bile duct into the duodenum undergoes a restriction, biliary secretion or pancreatic fluid may be prevented from flowing into the duodenum. This not only affects the digestion, but may cause jaundice, and hence, it has been the practice in the prior art to remove the restriction by a surgical operation. However, patients of an advanced age or who suffer from heart disease may not endure such operation. Recently, for those patients who are not amenable to such operation or where the restriction is caused by a temporary tumor which may be cured over a prolonged period of remedy, a remedy is attempted which utilizes an endoscope to place a cylindrical tube or prosthesis, formed of a synthetic resin material, into the affected part where the restriction has occurred, thus allowing the biliary secretion or pancreatic fluid to pass therethrough.

Such remedy will be briefly described with reference to FIGS. 1A to 1C. In FIG. 1A, there is shown an endoscope 1 including a forceps channel through which a guide wire 2 extends. The distal end 3 of the endoscope 1 is then inserted into coeloma. When the extremity 3a of the distal end 3 has reached an opening 4 of the duodenum, the guide wire 2 is push driven inward. The front end 2a of the guide wire 2 which projects forwardly from the extremety of the distal end is then forced into a restriction 5 to force it open until it completely extends through the restriction. A prosthesis 6 or a tube to be retained in place within the coeloma is then passed over the proximate end portion of the guide wire 2, followed by a pusher tube 7 which is utilized to drive the prosthesis inward. When the pusher tube 7 is driven inward, the prosthesis 6 moves along the guide wire 2 through the forceps channel of the endoscope 1 and reaches the location of the opening 4. As the pusher tube 7 is further driven inward, the prosthesis 6 is forced into the restriction 5 to force the walls of the restriction 5 apart, as shown in FIG. 1B. The inward drive applied to the pusher tube 7 ceases when the prosthesis has been inserted to a suitable position. The guide wire 2 is then withdrawn from the endoscope 1, and then the distal end 3 of the endoscope 1 is removed from the coeloma, thus leaving only the prosthesis 6 within the restriction 5. In this manner, biliary secretion or pancreatic fluid is allowed to flow through the prosthesis into the duodenum. In this manner, the risk involved with a surgical operation is avoided, and the pains caused to a patient are suppressed to a relatively low level.

However, the described remedy has a drawback in that the guide wire 2 must have a degree of rigidity which is required to allow it to be passed through the restriction 5. However, the rigidity or toughness may cause the front end 2a of the guide wire 2 to abut against the wall 8 of coeloma before it is passed through the restriction 5, as shown in FIG. 1C. Such abutment may cause the wall 8 to be injured by the front end 2a of the guide wire, and in worst cases, a risk arises that a hole may be pierced in the wall 8.

SUMMARY OF THE INVENTION

In view of the foregoing, it is an object of the invention to provide a method of and an apparatus for guiding a prosthesis which permits a prosthesis to be placed within a restriction of coeloma to ensure a free flow of body fluid, by facilitating the insertion of a guide member into a restriction without injuring the wall of the coeloma adjacent to an affected area.

According to the invention, a guide member may be readily passed through a restriction without injuring the wall of the coeloma, thus enabling a prosthesis to be placed in the restriction.

BRIEF DESCRIPTION OF THE DRAWINGS

FIGS. 1A to 1C are schematic illustrations of a conventional arrangement for guiding a prosthesis during its use; FIG. 1B being an enlarged view to illustrate the prosthesis which is passed through a restriction and FIG. 1C being an enlarged view which shows the front end of a guide wire abutting against the wall of the coeloma;

FIGS. 2A to 2C are an elevational section of an apparatus for guiding a prosthesis according to one embodiment of the invention, and fragmentary, enlarged cross sections thereof;

DETAILED DESCRIPTION OF PREFERRED EMBODIMENTS

Figure 3:
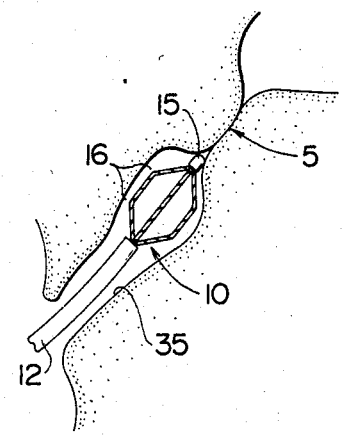
FIGS. 3 to 7 are schematic illustrations of the apparatus shown in FIGS. 2A to 2C as it is operated within the coeloma.

Referring to FIGS. 2A to 2C, there is shown an apparatus according to one embodiment of the invention. FIG. 2A is an elevational section, showing the general arrangement of the apparatus 11 for guiding a prosthesis. The apparatus 11 comprises a flexible sheath 12 which is adapted to be received in a forceps channel of an endoscope, not shown, a guide member 27 which is freely disposed within the flexible sheath 12, an operating unit 24 connected to the rear end of the guide member 27, and a basket assembly 10 connected to the distal end of the guide member 27.

The flexible sheath 12 comprises a flexible tube 13 which is adapted to be received in a forceps channel, not shown, and a fitting 21 connected to the rear end of the tube 13 and formed with a fluid inlet 19. Thus, a treatment fluid may be injected into the tube 13.

The guide member 27 comprises the basket assembly 10 which is formed by a plurality of resilient wires of reduced diameter which may be expanded into or shrunk from a cage configuration, an intermediate length 27b defined by a bundle of resilient wires, a detent 18 connected to an operating pipe 23 to be described later, and a resilient wire 27a extending to the proximate end which comprises one of the resilient wires mentioned above.

The basket assembly 10 is formed by a plurality of resilient wires 16 of reduced diameter, for example. The opposite ends of the wires are clamped together by a front end tip 15 and a rear end tip 17, respectively. A plurality of bends 16a are formed in each of the resilient wires 16 so as to define a cage-shaped wire basket when these wires are expanded. The front end tip 15 has a rounded extremety, which is effective to prevent the wall of the coeloma from being injured by such extremety when the guide member 27 is inserted into the coeloma. After being clamped together by the rear end tip 17, the resilient wires 16 extend in a bundle of an increased length to define the intermedite length 27b, the rear end of which is secured to an anchorage 18b of the cylindrical detent 18, as shown in FIG. 2B. A recess 18a is formed in the rear end of the detent 18, and only one of the resilient wires from the bundle extends rearwardly, substantially in alignment with the center axis of the recess 18a to form the proximate end resilient wire 27a.

The guide member 27 thus constructed is passed through the flexible sheath 12 and can be driven back and forth. Then the basket assembly 10 moves out of or into the distal end of the sheath 12, and during such movement, the entire basket assembly can be resiliently expanded or shrunk in a direction perpendicular to the axis of the guide member 27.

The construction of the operating unit 24 will now be described with reference to FIG. 2C. The operating unit 24 generally has a cylindrical, stepped configuration. Its front portion internally houses a guide block 31 in which a wire passage 29 is formed. An operating pipe 23 having an increased length is secured in the front end of the guide block 31, and extends forwardly through an opening 24c formed in the front wall of the unit 24. The combination of the operating pipe 23, the wire passage 29, a bore 24a formed in the rear portion of the operating unit 24, and an opening 24b at the rear end of the operating unit 24 defines a passageway which is continuous throughout these members. Female threads are formed in the top of the guide block 31, extending toward the wire passage 29. Threadably engaged with the female threads is a clamping screw 28 having a knob 25 at its head and which extends through an opening formed in the top of the operating unit 24. When the screw 28 is to be used to clamp the wire 27a of the guide member 27 within the operating unit 24, the operating pipe 23 is initially positioned by inserting its front end until it is fitted in and abuts against the recess 18a in the detent 18 (see FIG. 2B). The screw 28 may be then turned to hold the resilient wire 27a against the internal wall of the wire passage 29, thus securing it. In this manner, by tightening or loosening the screw 28, the operating unit 24 can be detachably mounted on the resilient wire 27a. The rear portion of the operating unit 24 is formed as a grip 26, which may be held by hand to move the entire operating unit along the guide member 27, thus opening or closing or expanding and shrinking the basket assembly 10 (see FIG. 2A).

It will be noted in FIG. 2A that an O-ring 22 is fitted between the fitting 21 and the operating pipe 23 in the region of an opening of the fitting 21, thereby providing a seal therebetween.

The operation of the apparatus will now be described with reference to FIGS. 3 to 7. When the apparatus 11 shown in FIG. 2A is used to place a prosthesis 33 in a restriction 5 of a bile duct 35, the rear end of the guide member 27 or the resilient wire 27a is inserted into the front end of the flexible sheath 12, and is passed therethrough until the basket assembly 10 is received within the flexible sheath 12. The rear end of the resilient wire 27a which projects out of the fitting 21 on the flexible sheath 12 is then inserted initially into the operating pipe 23 of the operating unit 24 while, the screw 28 is fully loosened. When the front end of the operating pipe 23 is fitted into the recess 18a formed in the detent 18, as shown in FIG. 2B, the screw 28 is tightened, thereby securing the resilient wire 27a within the wire passage 29. This provides an integral connection between the guide member 27 and the operating unit 24.

Figure 4:
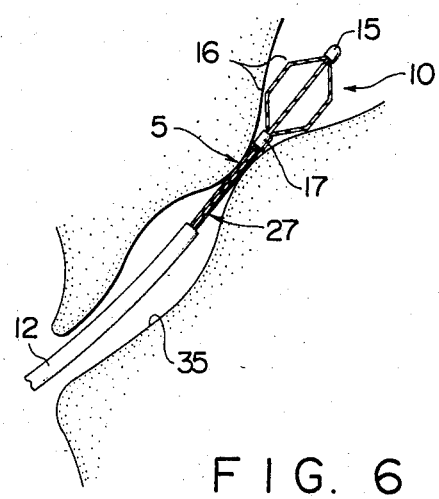

The apparatus is then inserted into the forceps channel of an endoscope, the distal end of which is inserted into the coeloma until the front end of the flexible sheath 12 extends into the bile duct 35 through the teat of the duodenum. After guiding the front end of the flexible sheath 12 to the proximity of the restriction 5, the operating unit 24 which is located externally of the forceps channel of the endoscope is manually held at its rear end, and is driven inward to cause an expansion of the basket assembly 10, as shown in FIG. 3, thus forcing the surrounding walls of the restriction 5 apart. The basket assembly is then closed or shrunk again. By repeating the expansion and the shrinkage of the basket assembly, the restriction 5 may be forced open to allow the guide member 27 to move past the restriction as shown in FIG. 4.

Figure 5:
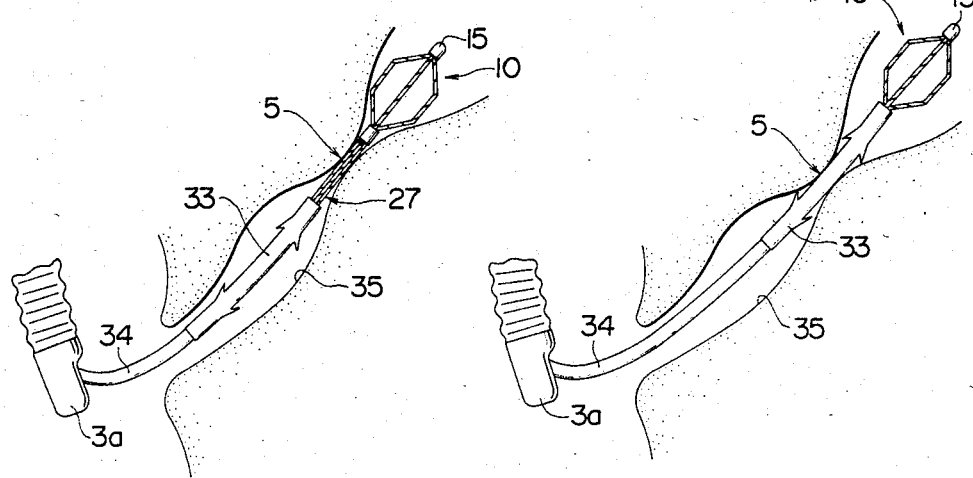
Figure 6:
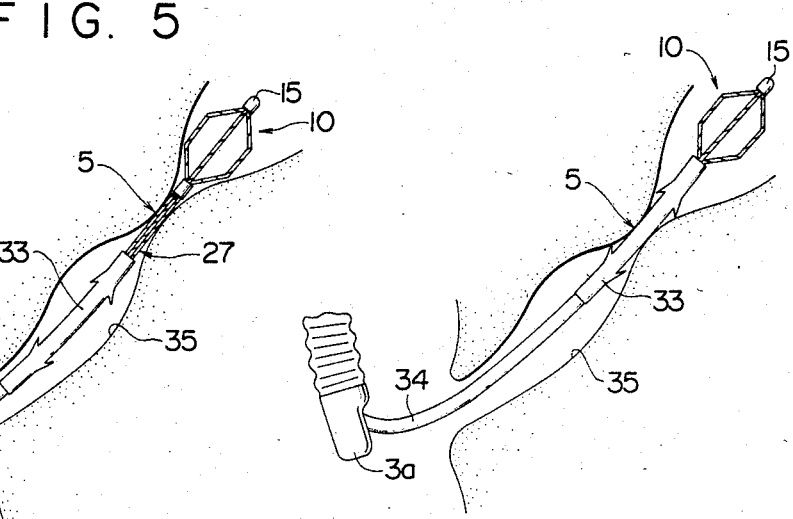

When the basket assembly 10 has moved past the restriction 5, the screw 28 is loosened while maintaining the basket assembly 10 open and then the operating unit 24 is withdrawn from the guide member 27. The flexible sheath 12 is then withdrawn from the forceps channel of the endoscope. However, since the guide member 27 has a length which is preferable equal to or greater than twice the length of the flexible sheath 12, it is possible to maintain the guide member 27 in the condition mentioned above while withdrawing the flexible sheath 12. While the guide member 27 is left in the coeloma as shown in FIG. 4, a prosthesis 33 and a pusher tube 34 are sequentially passed over the guide member 27 as shown in FIG. 5. By driving the pusher tube 34 inwardly, the prosthesis 33 may be inserted into the restriction 5, whereupon it may be placed within the restriction 5 as indicated in FIG. 6.

Figure 7:
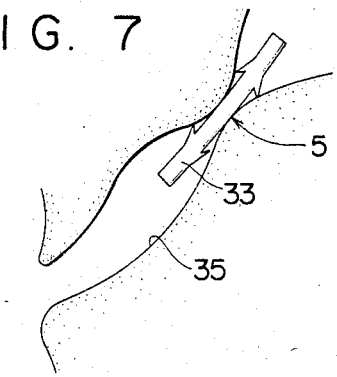

When the prosthesis 33 is retained in place, the basket assembly 10 is shrunk and is withdrawn from the coeloma together with the guide member 27, as is the endoscope. The ultimate result is the prosthesis 33 is left extending through the restriction 5 as indicated in FIG. 7. Under this condition, the prosthesis 33 is effective to displace biliary excretion which may accumulate within the bile duct 35.

It will be understood that with this embodiment, the rounded front end tip 15 is formed on the extremety of the basket assembly 10, and is passed through the restriction 5 while repeating its expansion and shrinkage, thus avoiding any undue stresses applied to the walls of the restriction. This prevents the likelihood that the walls of the coeloma may be injured.

It will also be noted that the operating unit 24 which causes an expansion and shrinkage of the basket assembly 10 is detachably mounted. This allows the flexible sheath 12 to be withdrawn from the guide member 27, thus permitting the basket forceps assembly to be utilized with the apparatus 11.

Since the guide member 27 or the wire 27a has a length which is equal to or greater than twice the length of the flexible sheath 12, the guide wire 27a may be held externally while withdrawing the flexible sheath 12 from the guide member 27, thus preventing the basket assembly 10 from being disengaged from the restriction 5.

In the description mentioned above, an expanding and shrinking construction is formed by the basket, by way of example, but it should be understood that any other alternate construction may be provided for the expanding and shrinking unit.

FIGS. 8 to 11 show a second embodiment of the invention in which similar parts to those mentioned above in connection with the first embodiment are designated by corresponding reference characters, and hence will not be described again.

Figure 8:
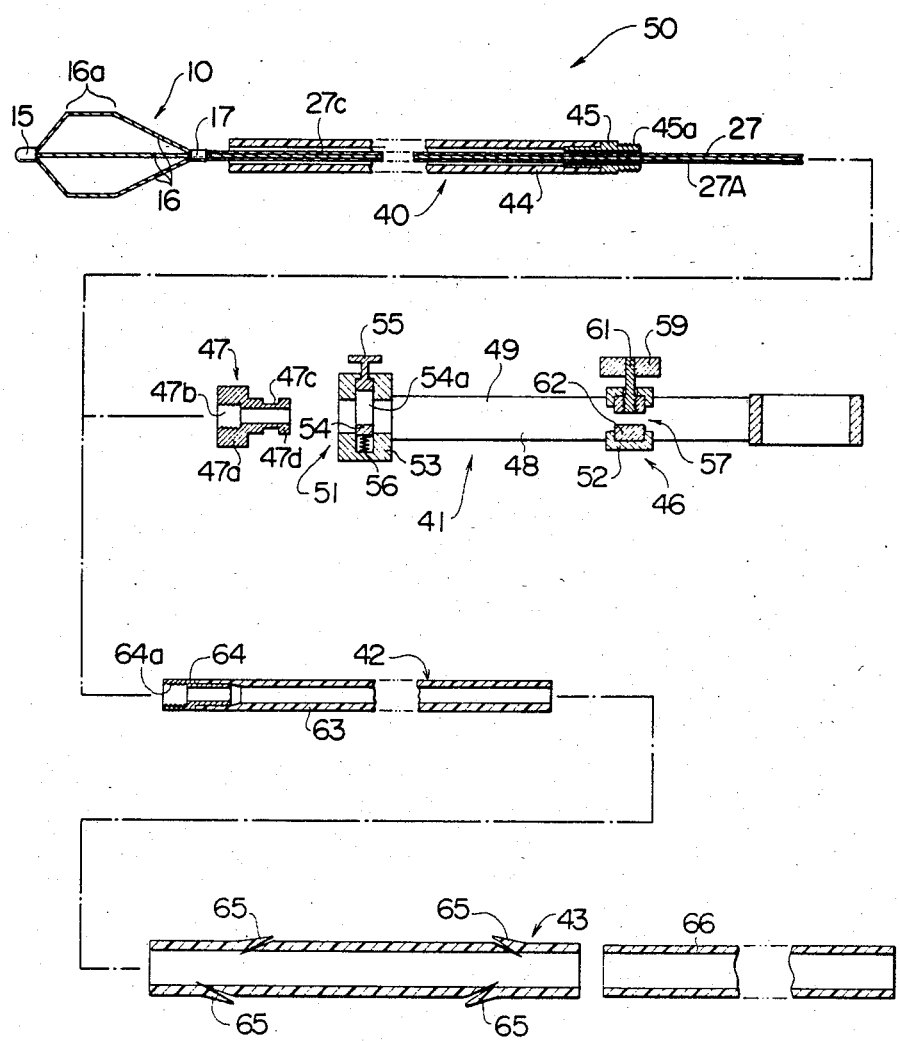
FIG. 8 is an elevational section of an apparatus for guiding a prosthesis according to a second embodiment of the invention.

In the embodiment shown in FIG. 8, an apparatus 50 for guiding a prosthesis comprises a guide member 27, a flexible sheath 40, an operating unit 41 which causes a movement of the guide member back and forth, a relay sheath 42, a prosthesis 43 and a pusher tube 66.

The guide member comprises a guide wire 27A and a basket assembly 10, which are constructed in quite the same manner as those shown in connection with the first embodiment, and a wire length 27c extending rearwardly from the rear end tip 17 which defines the basket assembly 10.

Figure 9:
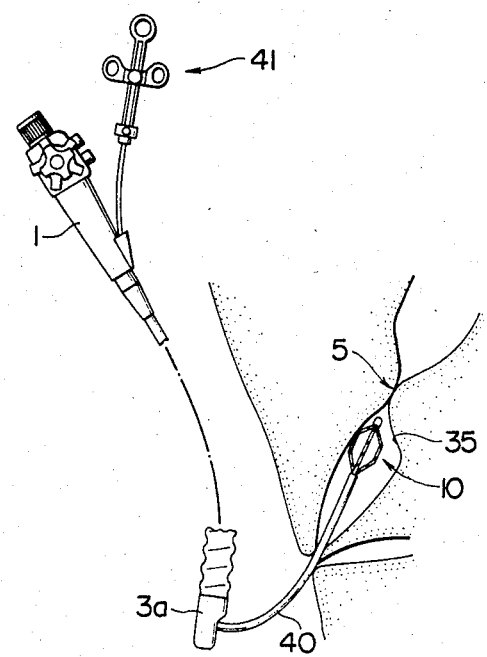
FIGS. 9, 10 and 11 are schematic illustrations of the apparatus shown in FIG. 8 as it is operated within the coeloma.
Figure 10:
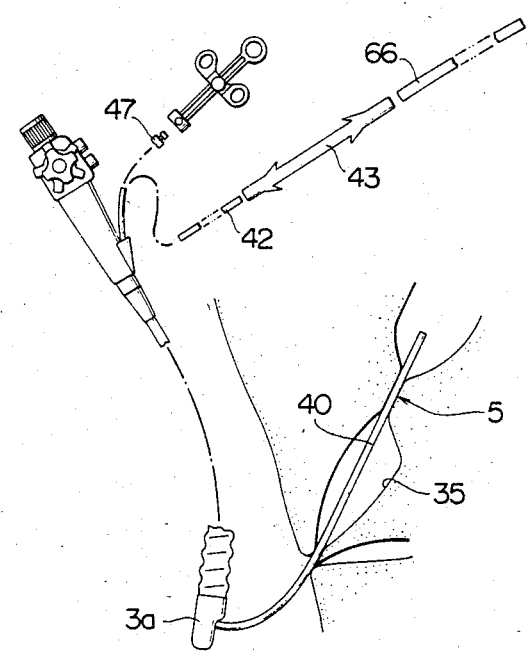

The flexible sheath 40 comprises a flexible tube 44 of an outer diameter which permits it to be received in the forceps channel of an endoscope 1 (see FIG. 9). A fitting 45 which is formed with male threads 45a is connected to the rear end of the tube 44. The guide wire 27A freely extends through the tube 44, and the operating unit 41 or the relay sheath 42 can be selectively connected to the rear end of the tube 44.

The operating unit 41, comprises an operating handle mechanism 46 of a sliding type, and a connector 47 which connects the mechanism 46 to the flexible tube 44. The connector 47 comprises a socket 47a, the front end portion of which is internally formed with female threads 47b for threadable engagement with the male threads 45a formed around the fitting 45, and the rear portion of which is integrally provided with a cylindrical engaging element 47d, the outer periphery of which is formed with an engaging groove 47c. The mechanism 46 includes a handle body 49 with a sliding rail 48 formed therein, and a tube fitting 51 which is attached to the front end of the body 49. A slider 52 is slidably engaged with the rail 48. More specifically, the tube fitting 51 includes a cylindrical support 53 having a bore in which a piston 54 having a through-opening 54a is disposed so as to be movable in a direction perpendicular to the body 49. The piston 54 is connected to an operator 55, while the body 49 also houses a coiled spring 56 which urges the piston 54 toward the operator 55. Accordingly, when the connector 47 is connected to the fitting 45 on the flexible tube 44 and then the engaging element 47d of the connector 47 is engaged with the through-opening 54a formed in the piston 54 which is then urged by the coiled spring 56, a connection is established between the flexible tube 44 and the body 49. The slider 52 includes a body 57 which is fitted with the rail 49. A shank 61 which can be axially translated by turning an operating knob 59 is disposed in the body 57, which also houses a receiver 62 which is adapted to engage the free end of the shank 61. In this manner, the rear end of the guide wire 27A which projects through the rear end of the flexible tube 44 may be clamped between the shank 61 and the receiver 62. Accordingly, the operating handle mechanism 46 which is detachably mounted on the rear end of the guide member 27 extending through the rear end of the flexible tube 44, may be used to move the guide wire 27A back and forth, thus causing the basket assembly 10 to project through the distal end of the flexible tube 44 so as to expand it in a direction perpendicular to the axis of the guide wire 27A or to cause it to shrink and be retracted into the tube 44.

The relay sheath 42 comprises an extension tube 63 of substantially the same diameter and the same length as the flexible tube 44. A tube fitting 64 is disposed on the free end of the extension tube 63 and is internally formed with female threads 64a which are adapted to threadably engage the fitting 45 on the flexible tube 44, thus allowing the extension tube 63 to be detachably connected in seriatim to the flexible tube 44.

The prosthesis 43 has a plurality of flaps 65 or barbs formed around its outer periphery to prevent its unintended withdrawal. The prosthesis 43 has an inner diameter which is greater than the outer diameters of the flexible tube 44 and the extension tube 63, and has an outer diameter which is less than the internal diameter of the forceps channel of the endoscope 1, thus allowing it to be passed over the flexible tube 44 and the relay sheath 42, serving as a guide and which are then connected together. In FIG. 8, the pusher tube 66 is shown as having internal and external diameters which remain the same as the prosthesis 43.

When the apparatus 50 is used to place the prosthesis 43 within the restriction 5 of the bile duct 35 of a living body, the operation begins with assembling the guiding apparatus in a condition which facilitates the insertion of the wire. Specifically, the connector 47 is connected to the fitting 45 on the flexible sheath 40. The guide wire 27A is then inserted into the flexible sheath 40 through the front end thereof until the basket assembly 10 is completely received therein. The connector 47 which is thus connected to the flexible sheath 40 has its engaging element 47a engaged with the tube fitting 51 on the operating unit 41 so as to be secured thereto. Thereafter, the rear end of the guide wire 27A which extends through the rear end of the flexible sheath 40 is secured to the slider 52 by turning the knob 59.

When the described assembly is completed, the flexible sheath 40 together with the guide wire 27A and the basket assembly 10 is inserted into the forceps channel of the endoscope 1. Subsequently, the distal end 3a of the endoscope 1 is inserted into the coeloma until the front end of the flexible sheath 40 is inserted into the bile duct 35 through the teat of the duodenum. Subsequently, by moving the operating unit 41 back and forth to open or close (to expand or shrink) the basket assembly 10, the front end of the guide wire 27A is driven into the restriction 5, as illustrated in FIG. 9. By utilizing the repeated opening or closing of the basket assembly 10 during the insertion process, both the guide wire 27A and the flexible sheath 40 may be brought to a position shown in FIG. 10 extending through the restriction 5 while avoiding the abutment of the front end of the guide wire 27A against the walls of coeloma which may injure them or avoiding the formation of any pierced opening. Thereafter the prosthesis 43 is placed within the restriction 5. In the first embodiment mentioned above, this placement required the withdrawal of the flexible tube 12, which may be a cumbersome operation.

Figure 11:
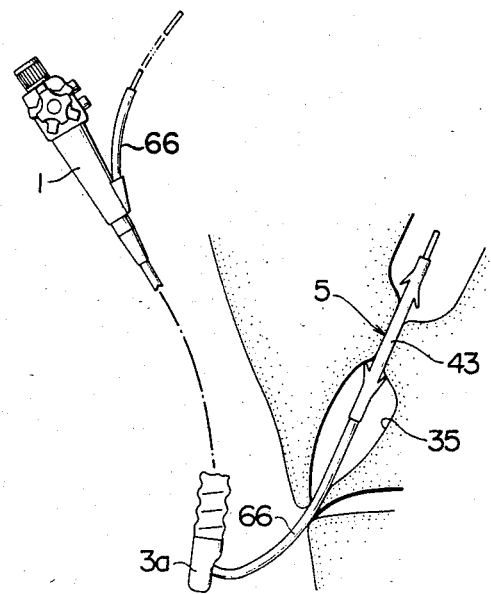

Alternately, an improvement in this respect is achieved with the present embodiment. Specifically, when the insertion of the guide wire 27A into the restriction 5 is completed, the knob 59 is turned to unlock the guide wire 27A, thus allowing the connector 47 to be disengaged from the flexible sheath 40. In this manner, the entire operating unit 41 is disconnected from the flexible sheath 40 and the guide wire 27A. The relay sheath 42 is then connected to the fitting 45 on the flexible sheath 40, and the prosthesis 43 and the pusher tube 66 are sequentially passed over the rear end of the relay sheath 42. By utilizing the relay sheath 42 and the flexible sheath 40 which are coupled together by the pusher tube 66 as a guide, the prosthesis 43 may be driven inward toward the restriction 5, thus allowing it to extend through the restriction 5 as shown in FIG. 11. After this, the guide wire 27A and the flexible sheath 40 and the relay sheath 42 which are coupled together are withdrawn from the endoscope 1, which is also withdrawn from the coeloma, thus leaving the prosthesis 43 in place within the restriction 5. It will be appreciated that the prosthesis 43 can be placed within the restriction 5 without requiring a withdrawal of the flexible sheath 40 which has been required in the first embodiment in the process of placing the prosthesis.

It will be understood that the likelihood that the walls of the coeloma may be injured is avoided in the present embodiment as in the first embodiment. Since it is unnecessary to withdraw the flexible sheath 40, there is no possibility that the guide wire 27A may be inadvertently disengaged from the restriction 5. The construction including the flexible sheath 40 and the relay sheath 42 which are coupled together for use as a guide to introduce the prosthesis into the restriction 5 allows a reduction in the overall length of the guide wire 27 and the flexible sheath 40. Specifically, the length may be similar to that of a treatment instrument used in an endoscope such as basket forceps, and a reduction in the resistance which is presented to the movement of the wire facilitates a movement of the guide wire 27A within the flexible sheath 40, thus allowing a reliable operation.

Figure 12:
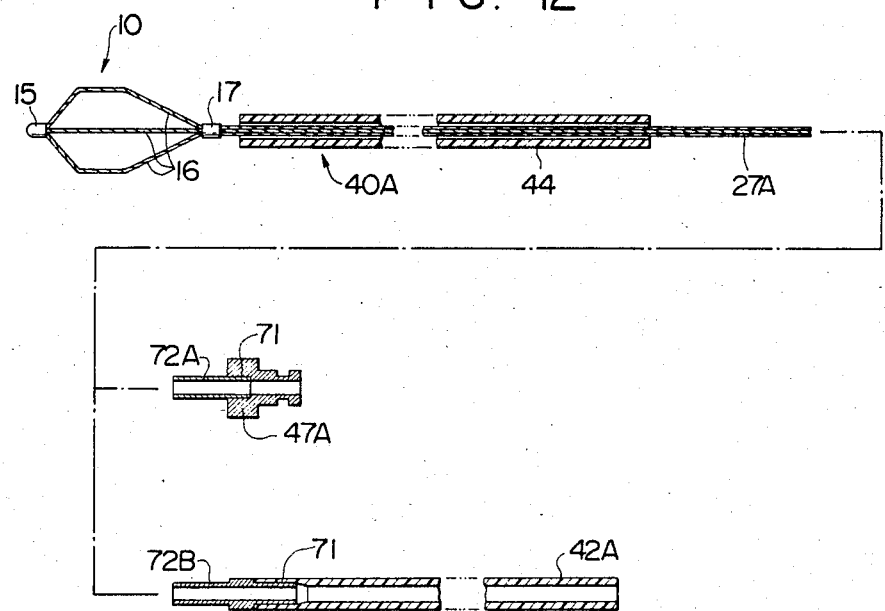
FIG. 12 is an elevational section of a modification of the apparatus shown in FIG. 8.

FIG. 12 shows a modification to the present invention. Specifically, a plug connection is utilized in connecting a connector 47A with a flexible sheath 40A or connecting a relay sheath 42A to the flexible sheath 40A. Specifically, the rear end of the flexible sheath 40A is left plain cut as it is molded while each of the connector 47A and a tube fitting 71 on the relay sheath 42A is provided with a tubular insert 72A or 72B having an outer diameter which is slightly greater than the internal diameter of the flexible sheath 40A so that a clearance fit is formed therebetween, thus allowing the connection or the disconnection to be achieved by a mere push-in or withdrawal of the inserts 72A and 72B into or from the flexible sheath 40A.

It should be understood that the invention is not limited to the embodiments described above. Specifically, the guide wire, the flexible sheath, the relay sheath and the pusher tube may be coiled in configuration. The operating unit may be provided with a water supply faucet which is disposed on the tube fitting. Alternatively, rather than providing a structure which may be operated by single hand, the handle body may be provided with a detachable knob to permit the arrangement to be operated with both hands. In addition, the prosthesis may be of a variety of currently available configuration including a pigtail having a loop or loops on either end or both ends.

What is claimed is:

1. A method of placing a prosthesis within a restricted passageway comprising the steps of:
   a first step of inserting the front end of a flexible sheath, containing a guide member such as a guide wire extending therethrough, to the proximity of a restriction within the restricted passageway;
   a second step of operating an operating unit which causes a movement of the guide member back and forth so as to open or close and thereby expand or shrink a resilient basket attached to the front end of the guide member and thereafter moving the basket past the restriction;
   a third step of leaving the guide member which has moved past the restriction in place within the passageway while withdrawing the flexible sheath out of the passageway;
   a fourth step of passing a prosthesis over the guide member, followed by passing a pusher tube over the guide member with, the pusher tube driving the prosthesis inward along the guide member;
   a fifth step of driving the pusher tube inward to place the prosthesis within the restriction; and
   a sixth step of withdrawing the guide member out of the passageway.

2. A method of placing a prosthesis within a restricted passageway comprising the steps of:
   a first step of inserting the front end of a flexible sheath, containing a guide member such as a guide wire extending therethrough, to the proximity of a restriction within the passageway;
   a second step of operating an operating unit which causes a movement of the guide member back and forth so as to open or close and thereby expand or shrink a resilient basket attached to the front end of the guide member and thereafter moving the basket past the restriction;
   a third step of leaving the flexible sheath within the passageway while disconnecting the operating unit from the flexible sheath;
   a fourth step of connecting a relay sheath to the flexible sheath which is left within the passageway;
   a fifth step of passing a prosthesis over the relay sheath, followed by passing a pusher tube over the relay sheath, so as to drive the prosthesis inward along the sheath;
   a sixth step of driving the pusher tube inward so as to place the prosthesis within the restriction; and
   a seventh step of withdrawing the flexible tube and the relay sheath through which the guide member extends from within the passageway.

3. A kit for placing a prosthesis within a restricted passageway, comprising:
   a flexible sheath which can be received in a forceps channel of an endoscope;
   a guide member freely extending through said flexible sheath;
   an operating unit detachably connected to the rear end of said guide member for causing a movement of said guide member back and forth;
   basket assembly means connected to the front end of said guide member and movable back and forth in response to an operating of said operating unit, said basket assembly means moving out of or into the front end of said flexible sheath in accordance with the movement of said guide member so as to expand or shrink said guide member as a whole in a direction perpendicular to the axis of said guide member;

a prosthesis to be placed at a given location using said guide member as a guide; and a pusher tube for driving said prosthesis along said guide member.

4. A kit according to claim 3 in which said flexible sheath has an external diameter which is less than the internal diameter of said prosthesis.

5. A kit according to claim 3 or 4 in which the rear end of said flexible sheath is adapted to be connected to a relay sheath having substantially the same diameter as said flexible sheath.

6. A kit according to claim 3, in which a portion of said guide member is inserted into said passageway through said endoscope and which is exposed externally of said endoscope has a length which is greater than the length of said flexible sheath.

7. A kit according to claim 3, in which said operating unit is detachably mounted on the rear portion of said guide member and is formed with a through-opening through which said guide member extends and in which said guide member is a resilient wire.

8. A kit according to claim 7, in which an operating pipe of a given length extends from said operating unit and communicates with the through-opening formed in said operating unit, thereby providing a passageway through which said guide member extends, and in which said guide member is a resilient wire.

9. A kit according to claim 3, in which said operating unit is mounted on the rear end portion of a resilient wire which functions as said guide member and extends through the rear end of said flexible sheath.

10. A kit according to claim 9, in which a connector is mounted on the front end of said operating unit and is constructed so as to permit its connection with said rear end of said flexible sheath.

11. A device for moving past a restricted passageway, comprising:

a flexible sheath which can be received in a forceps channel of an endoscope;

a guide member freely extending through the flexible sheath;

an operating unit detachably connected to the rear end of the guide member for causing a movement of the guide member back and forth; and basket assembly means connected to the front end of the guide member and movable back and forth in response to operation of the operating unit, said assembly means moving out of or into the front end of the sheath in accordance with the movement of the guide member so as to expand or shrink as a whole in a direction perpendicular to the axis of the guide member and thereby urge said basket assembly means past said restriction in said restricted passageway.

* * * * *